United States Patent [19]

Higgins

[11] Patent Number: 5,753,182
[45] Date of Patent: May 19, 1998

[54] METHOD FOR REDUCING THE NUMBER OF FREE RADICALS PRESENT IN ULTRAHIGH MOLECULAR WEIGHT POLYETHYLENE ORTHOPEDIC COMPONENTS

[75] Inventor: Joel Higgins, Claypool, Ind.

[73] Assignee: Biomet, Inc., Warsaw, Ind.

[21] Appl. No.: 601,080

[22] Filed: Feb. 14, 1996

[51] Int. Cl.$^6$ .................................................. A61L 2/08
[52] U.S. Cl. ................................. 422/23; 422/40
[58] Field of Search ........................ 422/22, 25, 23, 422/32, 40, 903

[56] References Cited

U.S. PATENT DOCUMENTS

| | | | |
|---|---|---|---|
| 3,887,669 | 6/1975 | Pillet | 264/16 |
| 3,905,376 | 9/1975 | Johnson et al. | 129/595 |
| 3,919,773 | 11/1975 | Freeman | 32/10 A |
| 3,923,740 | 12/1975 | Schmitt et al. | 260/47 UA |
| 3,955,566 | 5/1976 | Stoffey | 128/90 |
| 4,064,566 | 12/1977 | Fletcher et al. | 3/1.9 |
| 4,153,641 | 5/1979 | Deichert et al. | 260/827 |
| 4,207,286 | 6/1980 | Boucher | 422/22 |
| 4,214,578 | 7/1980 | Gianakakos et al. | 128/90 |
| 4,241,203 | 12/1980 | Wenzel et al. | 422/23 |
| 4,243,578 | 1/1981 | O'Sullivan et al. | 260/42.52 |
| 4,248,807 | 2/1981 | Gigante | 264/18 |
| 4,321,232 | 3/1982 | Bithell | 422/23 |
| 4,344,423 | 8/1982 | Evans et al. | 128/90 |
| 4,396,377 | 8/1983 | Roemer et al. | 433/199 |
| 4,396,476 | 8/1983 | Roemer et al. | 204/159.16 |
| 4,512,340 | 4/1985 | Buck | 128/90 |
| 4,656,236 | 4/1987 | Hudeček et al. | 526/264 |
| 4,698,373 | 10/1987 | Tateosian et al. | 522/95 |
| 4,720,319 | 1/1988 | Gasser | 156/273.5 |
| 4,782,118 | 11/1988 | Fontanille et al. | 525/286 |
| 4,793,330 | 12/1988 | Honeycutt et al. | 128/90 |
| 4,961,954 | 10/1990 | Goldberg et al. | 427/2 |
| 5,098,696 | 3/1992 | Montgomery | 424/61 |
| 5,098,977 | 3/1992 | Frautschi et al. | 527/313 |
| 5,100,689 | 3/1992 | Goldberg et al. | 427/2 |
| 5,137,448 | 8/1992 | Dougherty et al. | 433/214 |
| 5,280,015 | 1/1994 | Jacobson et al. | 514/46 |
| 5,290,548 | 3/1994 | Goldberg et al. | 424/78.18 |
| 5,306,293 | 4/1994 | Zacouto | 607/17 |
| 5,380,901 | 1/1995 | Antonucci et al. | 556/440 |
| 5,387,105 | 2/1995 | Dougherty et al. | 433/214 |
| 5,414,049 | 5/1995 | Sun et al. | 422/22 |
| 5,417,969 | 5/1995 | Hsu et al. | 422/22 |

OTHER PUBLICATIONS

McGraw-Hill Encyclopedia of Science & Technology, 6th Edition, vol. 7, pp. 400–403, 1987.

McGraw-Hill Encyclopedia of Science & Technology, 6th Edition, vol. 7, p. 402, 1987.

McGraw-Hill Encyclopedia of Science & Technology, 6th Edition, vol. 14, pp. 146–147, 1987.

McGraw-Hill Encyclopedia of Science & Technology, 6th Edition, vol. 15, p. 203, 1987.

McGraw-Hill Encyclopedia of Science & Technology, 6th Edition, vol. 17, pp. 410–411, 1987.

(List continued on next page.)

*Primary Examiner*—Thomas G. Wyse
*Attorney, Agent, or Firm*—Harness, Dickey & Pierce, P.L.C.

[57] ABSTRACT

A method for reducing the number of free radicals in an implantable medical component requiring sterilization includes the steps of packaging the component in an oxygen-resistant container, sterilizing the packaged component, and exposing the packaged and sterilized component to a gas capable of combining with free radicals. The step of packaging includes vacuum sealing the component in an oxygen barrier bag. The step of sterilizing includes exposing the packaged component to radiation such as gamma radiation. The step of exposing the packaged and sterilized component to a gas capable of combining with free radicals includes placing the packaged and sterilized component in a pressure vessel and introducing pressurized hydrogen gas into the vessel for a period of time.

23 Claims, 1 Drawing Sheet

OTHER PUBLICATIONS

Walter Y. Wen et al., "Radiation Chemistry of Polyethylene.XIII. Alkyl Radical Decay Kinetics in Single Crystalline and Extended–Chain Samples of Linear Polyethylene", *Macromolecules*, vol. 7, No. 2, pp. 199–204, 1974.

David R. Johnson et al., "Radiation Chemistry of Polyethylene.XII.Alkyl Radical Decay and Amorphous Content", *Journal of Physical Chemistry*, vol. 77, No. 18, pp. 2174–2179, 1973.

V.M. Patel et al., "Radiation Chemistry of Polyethylene.XIV.Allyl Radical Decay Kinetics in Different Types of Polyethylene", *Journal of Polymer Science* (Polymer Physics Edition), vol. 16, No. 3, pp. 467–484, 1978.

D.C. Waterman et al., "The Radiation Chemistry of Polyethylene.X.Kinetics of the Conversion of Alkyl to Allyl Free Radicals", *Journal of Physical Chemistry*, vol. 74, No. 9, pp. 1913–1922, 1970.

Rafil Basheer et al., "Radiation Chemistry of Linear Low–Density Polyethylene.I. Gel Formation and Unsaturation Effects", *Journal of Polymer Science* (Polymer Physics Edition), vol. 21, No. 6, pp. 949–956, 1983.

Rafil Basheer et al., "Radiation Chemistry of Linear Low–Density Polyethylene. II. Kinetics of Alkyl and Allyl Free–Radical Decay Reactions", *Journal of Polymer Science* (Polymer Physics Edition), vol. 21, No. 6, pp. 957–967, 1983.

T.S. Dunn et al., "Stability of γ–Irradiated Polypropylene II. Electron Spin Resonance Studies", *Advances in Chemistry Series*, vol. 169, pp. 151–158, 1978.

METHOD FOR REDUCING THE NUMBER OF FREE RADICALS PRESENT IN ULTRAHIGH MOLECULAR WEIGHT POLYETHYLENE ORTHOPEDIC COMPONENTS

BACKGROUND OF THE INVENTION

1. Field of the Invention

The present invention relates to limiting degradation of orthopedic components composed of polymers. More particularly, the present invention relates to a method for reducing the number of free radicals present in ultrahigh molecular weight polyethylene orthopedic components.

2. Description of the Related Art

The development of polymers over the last several years has enabled the extensive use of polymer-based materials as orthopedic devices. The great variety of biocompatible polymers also allows the manufacture of a remarkable array of implantable components from such polymers, including artificial organs, vascular tubing, and housings for mechanisms such as pacemakers.

While opening a new world of possibilities for medical treatment, the increased use of polymers in the biomedical arts has been attended by a unique set of problems not exhibited by metal. Specifically, most polymers are susceptible to some form of chemical degradation when exposed to any of several environmental elements.

Much of this degradation is the result of oxidation of the polymer which is initiated during the sterilization process by ionizing radiation. It is the step of irradiating the polymerized biocompatible component which forms free radicals which then serve as active sites to react with available ambient or in vivo oxygen.

Free radicals (or simply "radicals") are defined as compounds having one unpaired electron. One might be surprised to find that, in spite of the odd number of electrons, free radicals may, in fact, be relatively stable. The stability is provided by structure, for example in the case of the planar shape of trivalent carbon free radicals having seven valence electrons. Nitric oxide is an example of a stable free radical. Free radicals may also be unstable and chemically reactive in the case of, for example, the methyl radical.

Free radicals are involved in several types of reactions, such as addition reactions and in chain reactions where they often serve as intermediates. In chain reactions such as polymerization and combustion, free radicals are involved in the initiation and propagation components.

While having value in the polymerization process, free radicals become potentially problematic after polymerization is completed, and this is particularly true in biomedical applications. Specifically, free radicals serve as active sites to react with available oxygen. (Interestingly, free radicals may also crosslink with local polymer chains or may recombine with other radicals if oxygen or other reactive species are not present. Crosslinking in polymers is characterized by an increase in the insoluble fraction of the material, an increase in the creep resistance, and an improvement in the abrasion resistance of the material. To this end, it may be argued that crosslinking actually improves the characteristics of the polymer for use as an orthopedic bearing.)

The greater the number of free radicals, the greater the number of possible oxidation sites. Oxidation of several polymers (including the UHMWPE preferred for prosthetic bearings) results in a lowering of the molecular weight of the polymer as a result of polymer chain scission reactions. This lowering of the average molecular weight can also result in an increased level of crystallinity, density, and stiffness of the polymer. Oxidation reduces the mechanical strength and durability of several polymers, including UHMWPE.

The presence of a high density of free radicals is most troublesome because, in this radical-rich environment, an autoxidation reaction may begin. (Autoxidation is a self-catalyzed and spontaneous oxidation process which is often initiated by a free-radical generator.) Once initiated, this process is continuously fueled by oxygen from the surrounding atmosphere (ambient air or in vivo) as it diffuses into the material.

Free radicals may be generated by one of several ways. These include electric and microwave discharge and photochemical and thermal decomposition. As regards implantable medical components, however, it is another way of generating free radicals—irradiation—which is of primary concern.

Gamma rays and X-rays are forms of high-energy radiation that disrupt molecules and result in the generation of free radicals. This fact is unwelcome in the case of prosthetic bearings formed from polymers because high-energy radiation, particularly gamma rays, are frequently used in sterilization. Once exposed to such radiation, the free radicals form and, when combined with oxygen (available in both ambient air and in vivo), degradation may start. The quantity of free radicals produced is dependent upon the total irradiation dose the implantable component receives (which may be as high as 10.0 MRad), as the higher the absorbed dosage the more active sites are created. If oxidation begins while there is a high density of free radicals, the above-discussed autoxidation process is initiated that is continually fueled by oxygen from the surrounding atmosphere as it diffuses into the material.

Several packaging and processing modifications have been tried in an effort to reduce the potential oxidation of the various implantable medical components. These methods include forming the component under a vacuum or an inert gas environment, controlling maximum process temperatures, and implementing alternative sterilization processes such as ethylene oxide and plasma vapor. Efforts to reduce the potential oxidation of the various implantable medical components have also included exposure of the component to hydrogen gas at various pressures after irradiation. However, these methods have not proved satisfactory and, accordingly, an improved method of reducing potential oxidation of implantable medical components remains wanting.

SUMMARY OF THE INVENTION

It is therefore an object of the present invention to provide a method for reducing the number of free radicals in an implantable medical component such as a prosthetic bearing that overcomes the problems and deficiencies of known methods by providing a method that is safe and effective.

It is a further object of the present invention to provide such a method which provides for the packaging of the component in a container which serves as an oxygen barrier so as to prevent exposure of oxygen to ambient air prior to the implanting of the component on the patient.

It is an additional object of the present invention to provide such a method which incorporates sterilization through gamma radiation.

It is a further object of the present invention to provide such a method that combines free radicals with hydrogen gas to thereby extinguish the radicals.

3

The implantable medical component referred to herein may be virtually any article formed from a polymerized material for which sterilization is required, although the method of the present invention has a particular application in reducing the number of free radicals in a prosthetic component such as a bearing. (Bearing surfaces are naturally susceptible to wear in use. Accordingly, any degradation of the bearing surface through oxidation is particularly undesirable in such an application.)

The method of the present invention includes several steps.

The implantable component or, more particularly, the bearing, is initially formed by machining from an isostatically molded bar stock of a polymerized material, such as a polypropylene or a polyethylene. Alternatively, the component may be formed by any of several processes, including sheet molding, ram extrusion, or direct compression molding. The preferred polyethylene is ultrahigh molecular weight polyethylene, or UHMWPE. Once formed, the component is positioned in a bag that is impermeable to oxygen but is permeable to hydrogen. The bag is flooded with an inert gas such as argon or nitrogen which is then removed leaving a vacuum. The bag is then sealed.

The packaged component is sterilized through radiation. A preferred (but not exclusive) method of irradiating the component is through exposure to gamma rays. The packaged and irradiated component is then positioned in a pressure vessel. A pressurized gas, such as hydrogen, is then introduced into the vessel at a pressure above one atmosphere. Gas pressure and exposure time are controlled so as to allow adequate diffusion of the gas into the component, forcing the hydrogen and free radicals to combine, thus reducing the number of free radicals. The component is removed from the pressure vessel following the selected amount of time, the amount of time and the pressure of the vessel being dependent upon the density of free radicals in the component following irradiation.

Immersion in pressurized hydrogen gas extinguishes the free radicals by diffusing into the material during the immersion phase, thus causing the gas to become combined with the free radicals. The level of peroxy and alkyl radicals remaining in the polymer after exposure to the hydrogen gas is greatly reduced if not entirely eliminated.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which.

DETAILED DESCRIPTION OF THE PREFERRED EMBODIMENT

The drawings disclose the preferred embodiments of the present invention. While the configurations according to the illustrated embodiments are preferred, it is envisioned that alternate configurations of the present invention may be adopted without deviating from the invention as portrayed. The preferred embodiments are discussed hereafter.

Briefly, the method of the present invention for reducing the number of free radicals in a medical implantable component includes the steps of packaging the component in an oxygen-resistant/hydrogen gas permeable container, sterilizing the package component, and exposing the packaged and sterilized component to hydrogen gas or to a gas mixture containing hydrogen. According, the apparatus of the present invention includes a packaging component, a sterilizing component, and a pressuring component.

Figure 1:
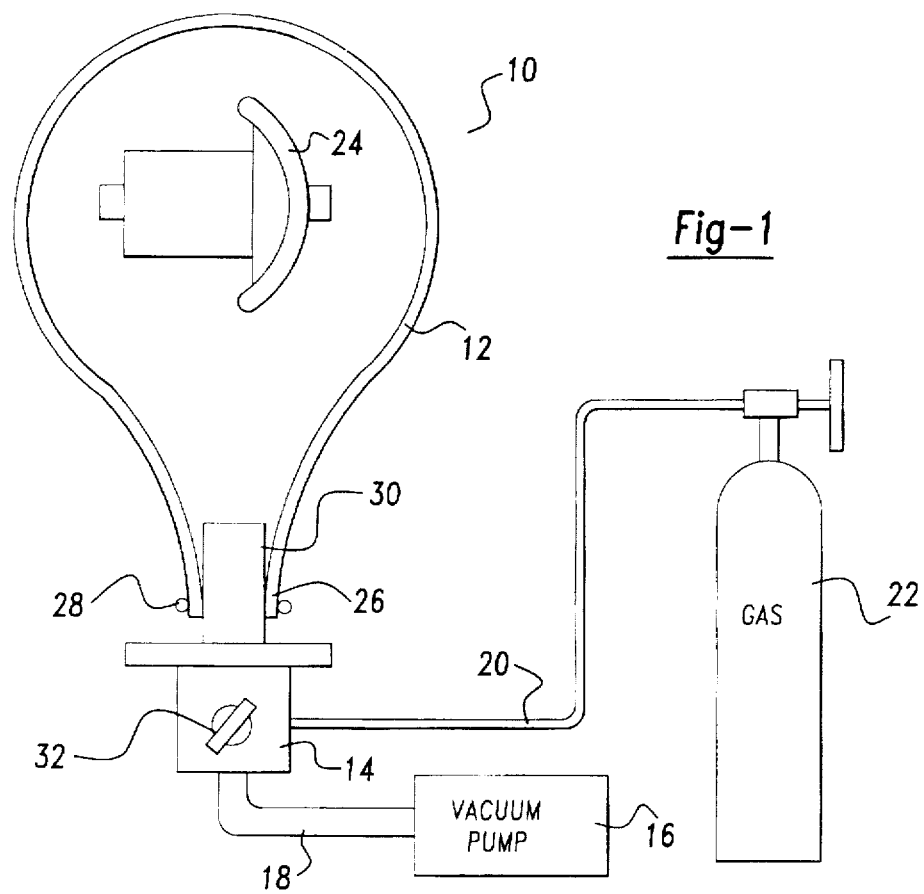
FIG. 1 is a diagrammatic view of an prosthetic bearing construction positioned within an oxygen barrier package.

Referring to FIG. 1, a diagrammatic view of a packaging component, generally illustrated as 10, is shown. The packaging component 10 includes an oxygen-resistant package 12, an adapter 14, a vacuum pump 16, a vacuum line 18, a gas line 20, and an inert-gas source 22.

Positioned within the package 12 is an implantable medical component 24. While the illustrated component 24 is a generic prosthetic bearing, it is to be understood that the component 24 may be any component composed of a polymerized material that is intended for implantation within the body as a part of a medical procedure and requires irradiating sterilization prior to implantation. Accordingly, the component 24 may be an artificial organ, vascular tubing, and housings for mechanical units such as pacemakers. However, the method according to the presenting invention finds particular application in situations where movement between two or more contacting surfaces is required, such as between bearing surfaces of a prosthetic implant.

The component 24 may be formed from one of several suitable polymers accepted for biological applications, although the polymer of a particularly concern is one that is commonly used for prosthetics, namely ultrahigh molecular weight polyethylene. (The polymers having high molecular weights demonstrate a particular susceptibility to degradation due to oxidation.) Where the component 24 is a prosthetic implant such as a bearing or related part, it is generally machined from isostatically molded bar stock.

The package 12 is selected for its ability to be substantially impermeable to oxygen while being substantially permeable to hydrogen. Accordingly, the package 12 may be an oxygen barrier bag or a glass-lined oxygen barrier bag. (A package demonstrating selective permeability such that it is suitable for application in the present method is manufactured by Stephen Gould, Inc. [Indiana], and is identified as 1P1C double-layer, 48 gauge, PET $SiO_2$-coated adhesive, 2-mil LLDPE.)

The component 24 is generally positioned within the package 12 through an open end 26 which is fitted to the adapter 14. A removable sealing member 28 (or other attachment) is provided for temporarily fastening the open end 26 of the package 12 to a nozzle 30 of the adapter 14.

Fitted to the adapter 14 is the gas line 20 which fluidly connects the inert gas source 22 with the adapter 14. Also fitted to the adapter 14 is the vacuum line 18 which fluidly connects the inert gas source 22 to the adapter 14. The adapter 14 includes a valve 32 which is operable to be moved between a closed position, an inlet position between the nozzle 30 and the gas line 20, and an outlet position between the nozzle 30 and the vacuum line 18.

The packaging component 10 is operated as follows. The implantable medical component 24 is positioned within the package 12, after which the open end 26 of the package is positioned on the nozzle 30. The sealing member 28 is thereafter positioned so as to form a fluid-tight seal between the open end 26 of the package 12 and the nozzle 30. The valve 32, which is normally maintained at its closed position, is turned to the inlet position such that inert gas flows under pressure from the source 22, through the line 20, and into the package 12. The inert gas may be argon, nitrogen or a similar gas.

Once the inside of the package 12 is flooded with the inert gas, the valve 32 is moved to its outlet position and the vacuum pump 16 is operated to create a vacuum within the package 12. After the inert gas is evacuated from the package 12, a vacuum-sealed, packaged component 34 (shown in FIG. 2) results. The valve 32 is returned to its closed position and the vacuum pump 16 is shut off. The packaged component 34 may be placed in an additional package such as a double-blister pack-box combination (not shown). This additional packaging is useful and generally necessary for transit and storage.

Figure 2:
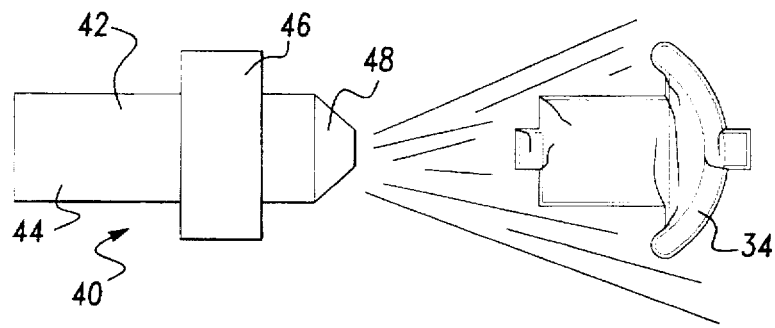
FIG. 2 is a diagrammatic view of the packaged prosthetic bearing in position before an irradiating unit.
Figure 3:
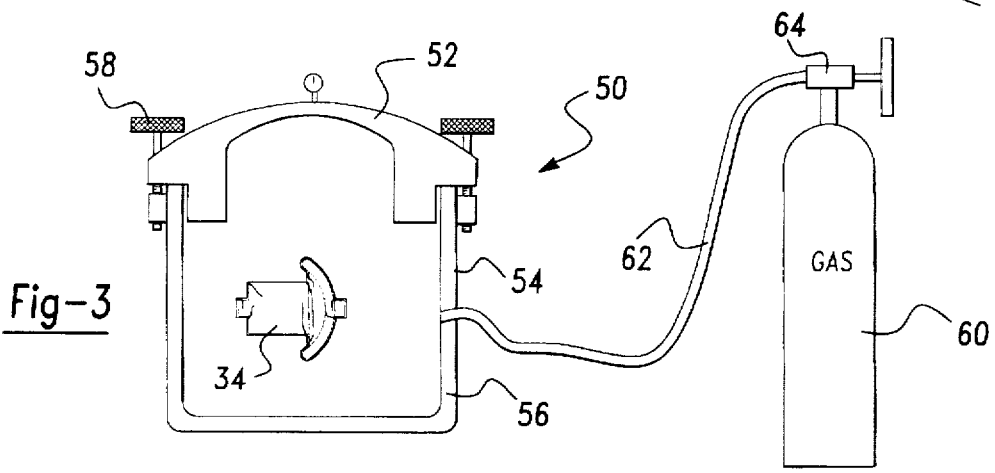
FIG. 3 is a diagrammatic view of the packaged and irradiated prosthetic bearing positioned within a pressure vessel.

Referring to FIG. 2, a sterilizing component 40 is shown and generally includes an irradiating unit 42. The irradiating unit 42 includes a radiation source portion 44, a beam focusing portion 46, and a beam outlet 48. The irradiating unit 42 produces high-energy radiation such as gamma radiation. (Electron beam radiation may also be used, although experiments have shown that it is difficult to identify a dosage that is effective on both metal and plastic, two materials commonly found in a single component.) The intensity of the radiation beam may be varied according to the size and shape of the component. The time of exposure is also variable, and depends on a variety of factors, including the age of the gamma source. (Age of the source may lead to a 10 percent variation of the exposure window.) In any event, radiation exposure time is generally between 2.2 to 2.9 hours. The object is a total absorbed dose of between 2.5 MRad and 3.8 MRad, with a limit of about 4.0 MRad.

Following the sterilization process by the sterilizing component 40, the packaged (and now irradiated) component 34 is gassed with hydrogen using the pressuring component 50. More particularly, the sealing cover 52 of a pressure vessel 54 is removed from a base portion 56. The component 34 is positioned within the base portion 56 of the vessel 54, and the cover 52 is returned and locked into place by locking fasteners 58. The pressure vessel 54 is connected to a hydrogen gas source 60 by a feed line 62. A valve 64 is fitted between the gas source 60 and the feed line 62. Normally in its closed position, the valve 64 is moved to its open position to allow hydrogen gas under pressure to enter the pressure vessel 54.

The total radiation dose (as determined by exposure time and beam intensity received by the material determines the quantity of free radicals produced in the material. The pressure of the hydrogen gas and the duration of exposure to the gas are accordingly functions of the density of free radicals present in the component 34. However, the pressure of the hydrogen gas within the pressure vessel 54 is preferably elevated to approximately 3 atm of pressure or above. The component 34 is exposed to this amount of pressure for several hours, with 6 hour exposure being suitable. Again, pressure and exposure ar variable and are adjusted according to the requirements of the particular irradiated component.

The presence of remaining free radicals in the package, sterilized, and gassed component 34 may be evaluated according to techniques such as electron spin resonance (ESR) testing. In addition to ESR testing, tensile evaluation with various strain rates may also be conducted on the prepared component.

The packaged, sterilized, and gassed component may be held for storage or may be distributed for use. The method according to the present invention reduces the risk of oxidative damage resulting upon exposure to in vivo and ambient environments.

It should be understood that while the packaging component 10, the sterilizing component 40, and the pressurizing component 50 have been illustrated in the various figures and discussed above as being separate components, it is conceivable that a single unit could well be formed which incorporates all three components. Accordingly, the apparatus as presented above is set forth for illustrative purposes and is not intended as being limiting.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A method for reducing the number of free radicals present in a component requiring sterilization, the method including the steps of:

packaging the component in a barrier material that is substantially impermeable to oxygen;

irradiating the packaged component; and exposing the packaged and irradiated component to a gas having a valence of 1 that is combinable with free radicals.

2. The method for reducing the number of free radicals of claim 1, including the step of packing the component in a material that is substantially impermeable to oxygen but is substantially permeable to said gas.

3. The method for reducing the number of free radicals of claim 1, including the step of substantially removing all gas from between the barrier material and the component during the step of packaging.

4. The method for reducing the number of free radicals of claim 1, including the step of positioning the component in a barrier material defined by a sack having one open end.

5. The method for reducing the number of free radicals of claim 1, including the step of positioning the packaged and irradiated component in a pressure vessel.

6. The method for reducing the number of free radicals of claim 5, including the step of exposing the packaged and irradiated component to gas that has a pressure greater than that of ambient air.

7. The method for reducing the number of free radicals of claim 1, including the step of exposing the packaged and irradiated component to hydrogen gas.

8. The method for reducing the number of free radicals of claim 1, including the step of irradiating the component with gamma radiation.

9. A method for reducing the number of free radicals present in a component requiring sterilization, the method including the steps of:

substantially removing ambient gases from around the component;

sterilizing the component; and exposing the component to a gas having a valence of 1 that is with the free radicals.

10. The method for reducing the number of free radicals of claim 9, including the step of positioning the component in an oxygen barrier container before removing said ambient gases.

11. The method for reducing the number of free radicals of claim 10, wherein said container has an inside, the method including the steps of flooding the inside of said container with an inert gas then substantially removing said inert gas from said inside of said container.

12. The method for reducing the number of free radicals of claim 9, including the step of sterilizing the component through exposure to radiation.

13. The method for reducing the number of free radicals of claim 12, including the step of sterilizing the component through exposure to gamma radiation.

14. The method for reducing the number of free radicals of claim 9, including the step of vacuum-sealing the component in a container which is substantially resistant to the inflow of oxygen.

15. The method for reducing the number of free radicals of claim 9, including the step of exposing the component to hydrogen gas.

16. The method for reducing the number of free radicals of claim 15, including the step of positioning the sterilized component in a pressure vessel.

17. The method for reducing the number of free radicals of claim 16, including the step of exposing the sterilized component to said hydrogen gas wherein said gas is at a pressure greater thin one atmosphere.

18. The method for reducing the number of free radicals of claim 9, including the step of forming the component from an isostatically molded material.

19. A method for reducing the number of free radicals present in a component requiring sterilization, the method including the steps of:

positioning the component within an oxygen barrier container;

substantially evacuating gases from said container;

sealing said container to form a packaged component;

sterilizing said packaged component; and combining the free radicals with non-radical molecules.

20. The method for reducing the number of free radicals of claim 19, including the step of exposing said packaged component to hydrogen gas.

21. A product produced by the process of claim 1.

22. A product produced by the process of claim 9.

23. A product produced by the process of claim 19.

* * * * *